US008861684B2

(12) United States Patent
Al-Kofahi et al.

(10) Patent No.: US 8,861,684 B2
(45) Date of Patent: Oct. 14, 2014

(54) FORWARD- AND VARIABLE-OFFSET HOOP FOR BEAM SCANNING

(75) Inventors: Omar Al-Kofahi, Chelmsford, MA (US); Peter J. Rothschild, Newton, MA (US)

(73) Assignee: American Science and Engineering, Inc., Billerica, MA (US)

( * ) Notice: Subject to any disclaimer, the term of this patent is extended or adjusted under 35 U.S.C. 154(b) by 253 days.

(21) Appl. No.: 13/585,157

(22) Filed: Aug. 14, 2012

(65) Prior Publication Data

US 2013/0064353 A1 Mar. 14, 2013

Related U.S. Application Data

(60) Provisional application No. 61/533,407, filed on Sep. 12, 2011.

(51) Int. Cl.
*G21K 1/02* (2006.01)
*G21K 1/04* (2006.01)
*H01J 35/00* (2006.01)

(52) U.S. Cl.
CPC *G21K 1/043* (2013.01); *H01J 35/00* (2013.01)
USPC .......................................... 378/147; 378/160

(58) Field of Classification Search
CPC ............ G21K 1/02; G21K 1/043; H01J 35/00
USPC .......................... 378/119–121, 145–147, 160
See application file for complete search history.

(56) References Cited

U.S. PATENT DOCUMENTS 6,418,194 B1 7/2002 McPherson et al. .......... 378/160
6,434,219 B1 * 8/2002 Rothschild et al. .......... 378/160
7,218,704 B1 5/2007 Adams et al. .................. 378/57
7,593,510 B2 9/2009 Rothschild .................... 378/160
2006/0245547 A1 11/2006 Callerame et al. ............ 378/160

FOREIGN PATENT DOCUMENTS

WO WO 2007/111672 A2 10/2007 ............... G21K 5/04

OTHER PUBLICATIONS

Kalvas et al., "Fast slit-beam extraction and chopping for neutron generator," *Rev. Sci. Instrum.*, vol. 77, No. 3, Proceedings of the 11*th* International Conference on Ion Sources / Beam Extraction, pp. 03B904-1-03B904-3 (2006).

Tae Hoon Kim, Authorized officer Korean Intellectual Patent Office, International Search Report—Application No. PCT/US2012/050722, mailing date Mar. 4, 2013 (4 pages).

* cited by examiner

*Primary Examiner* — Courtney Thomas
(74) *Attorney, Agent, or Firm* — Sunstein Kann Murphy & Timbers LLP

(57) ABSTRACT

An apparatus for forming a beam of energetic particles and for scanning the beam of particles with respect to an inspected object. The apparatus has a source of energetic particles characterized by an effective beam origin and a rotating hoop having at least one aperture, such that the effective beam origin of the source is closer to the inspected object than the axis of rotation of the rotating hoop. A collimating structure disposed interior to the rotating hoop collimates emission by the source into a fan beam prior to impinging on the rotating hoop. In some embodiments, the effective beam origin may be moved with respect to the axis of rotation of the hoop.

5 Claims, 4 Drawing Sheets

27
5"
20
19
22
15

FORWARD- AND VARIABLE-OFFSET HOOP FOR BEAM SCANNING

The present application claims the priority of U.S. Provisional Patent Application Ser. No. 61/533,407, filed Sep. 12, 2011, which is incorporated herein by reference.

TECHNICAL FIELD

The present invention relates to an apparatus for scanning a beam of penetrating radiation, and more particularly to apparatus in which a source of penetrating radiation is disposed within a rotating hoop.

BACKGROUND ART

Beams of energetic particles are routinely temporally modulated and/or swept in a direction by means of a rotating structure which attenuates the beam other than when it emanates from one or more apertures within the structure during a portion of the rotation of the structure. An example of such an application of beam chopping is described by McPherson et al., A new high-speed beam chopper for time-resolved X-ray studies, *J. Synchrotron Rad.*, vol. 7, pp. 1-4 (2000), which is incorporated herein by reference. In various applications, a small opening in such a rotating structure is swept across an internal beam that has a substantial opening angle, with the effect of scanning an emergent beam of small cross-section, such as a pencil beam, across some region of solid angle. In particular, rotating hoops have been used to create flying spot x-ray beams that can be used to create x-ray backscatter images. When the rotating structure has a substantially cylindrical symmetry about its axis of rotation, the rotating structure may be referred to as a "hoop."

In hoops used for scanning energetic beams, the source is typically disposed centrally, substantially coincident with the axis of rotation of the rotating hoop, as in Kalvas, et al., Fast slit-beam extraction and chopping for neutron generator, *Rev. Sci. Instruments*, vol. 77, 03B904 (2006).

For sources that produce penetrating radiation in a conical beam, a first collimator is disposed proximate to the source itself, to collimate the beam substantially into a plane (or into a fan beam with a small divergence parallel to the fan). A rotating hoop then collimates the beam in a direction tangential to the fan beam, so that a pencil beam emerges. Openings in the hoop may then be shaped as slits, circular or elliptical apertures, or other shapes, in order to collimate the beam in the direction tangential to the direction of hoop rotation. The distance between the focal spot of the source and the aperture is ideally as large as possible in order to minimize the divergence of the beam with increasing distance. However, this must be balanced with the desire to make the hoop itself as small as possible, to minimize the moment of inertia of the rotating structure and to keep the dimensions of the apparatus as small as possible A hoop 10 typically employed in x-ray inspection is shown in FIG. 1, in cross-section taken in a plane transverse to axis of rotation 11. Hoop 10 has three apertures 12 located in rim 13, and creates a beam (not shown) that can scan over an approximately 86-degree field of view (FOV) 19. Penetrating radiation emanates from a source 15 of penetrating radiation, typically as Bremsstrahlung radiation from a small region of a target to which electrons from an electron gun have been accelerated. The plane 9 from which penetrating emission is emitted, such as the plane of a Bremsstrahlung target, will be referred to herein as the "effective emission plane," and the region of emission will be referred to as the "effective beam origin" 8. The source 15 of penetrating radiation, such as an x-ray tube (as measured from the effective emission plane), is offset from the central axis 11 of the 12-inch hoop in the reverse direction (i.e. away from an object 16 being scanned) by an offset distance 17 (here, 5 inches) (i.e., away from an object 16 being scanned) in order to increase the collimation distance 18 between the x-ray focal spot in the tube and the aperture in the rim of the hoop that defines the beam. For heuristic convenience, source 15 may be referred to, herein and in any appended claims, as a "tube" or an "x-ray tube," but it is to be understood that the invention is not limited thereby.

Rearward offset of the source relative to axis of rotation 11 of a beam-chopping hoop 10 has been required for x-ray inspection applications, because x-ray tubes that operate with a power greater than about 1.5 kW have in the past typically had focal spot sizes on the order of about 3 mm in diameter. Since smaller beam sizes are indicated for inspection purposes, the source must be sufficiently offset in the reverse direction with respect to the axis of rotation 11 of hoop 10 to maximize collimation distance 18 and allow for extinction of radiation from the perimeter of the beam so that a beam with a sufficiently "trimmed" cross section is incident on the object 16 being inspected. The beam cross section would become too large for the typical distance of five feet to the object 16 being inspected if the focal spot was positioned closer to the aperture, resulting in low-resolution, and therefore low-quality backscatter images being produced One problem with the prior art reverse-offset hoop depicted in FIG. 1 is that the field of view 19 for a hoop with three apertures with the offset shown is limited to less than 90 degrees. Additionally, the maximum speed at which a hoop of a particular mass can be rotated is limited by stresses on the outer rim of the hoop. For example, for a hoop capable of collimating x-rays in the 180 keV range, rotation of the hoop is practically limited to about 3600 rpm. An implication of that limitation is that for a system that uses three such hoops that are interleaved temporally (i.e., only one of the three hoops produces an active x-ray beam at any given time, as in a three-sided inspection portal, for example), the image created from any one of the hoops is limited to less than 20 lines/second. A more typical hoop speed of 2600 rpm for a 225 keV system produces only 14 image lines/second. This image acquisition rate is much too slow for scanning vehicles moving more than about 5 km/hr. In the case of a hoop with six apertures rotating at 3600 rpm, while the image acquisition rate is increased from 20 to 40 lines/second, the FOV for such a reverse-offset hoop is correspondingly reduced to about 39 degrees, insufficient for many applications.

A beam chopping apparatus that would allow for faster scan rates for substantial fields of view is, therefore, highly desirable.

SUMMARY OF EMBODIMENTS OF THE INVENTION

In accordance with embodiments of the present invention, an apparatus is provided for forming a beam of energetic particles and for scanning the beam of particles with respect to an inspected object. The apparatus has a source of energetic particles characterized by an effective emission plane, an effective beam origin, and a rotating hoop having at least one aperture, the rotating hoop characterized by an axis of rotation. A collimating structure is disposed interior to the rotating hoop for collimating emission by the source into a fan beam prior to impinging on the rotating hoop. The effective beam origin of the source is closer to the inspected object than the axis of rotation of the rotating hoop.

In accordance with another embodiment of the invention, the effective beam origin may be a target of an x-ray tube. The effective beam origin may also be adapted to be moved with respect to the axis of rotation of the rotating hoop.

In further embodiments of the invention, the collimating structure may include a plurality of moveable shielding devices, such as rotatable shielding arms, for varying an angle of the fan beam emitted from the collimating structure.

In yet further embodiments of the invention, the effective beam origin may be adapted to be moved with respect to the axis of rotation of the rotating hoop during the course of inspection operation.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS OF THE INVENTION

Definitions

As used herein and in any appended claims, the term "particles" may be characterized by mass (e.g., baryons, such as neutrons, or leptons, such as electrons), or may refer to electromagnetic radiation, i.e., photons, in which case they are massless. The term "penetrating radiation" refers to radiation of sufficient energy per particle to penetrate materials of interest to a substantial and useful degree and include x-rays and more energetic forms of radiation. Such particles may be referred to herein as "energetic particles." For convenience, the term "x-ray" may be used, without limitation, as an example of penetrating radiation.

The term "collimation length" refers to the distance from the focal spot of an x-ray tube, or other source, to the defining aperture in the rim of the hoop.

In recent years, x-ray tubes at energies above 150 keV have become available that have a focal spot (about 1.0-1.5 mm) sufficiently small as to allow collimation distances to be reduced. Thus, non-offset or forward-offset hoops may be used while maintaining a beam with acceptably small cross section at typical inspection distances.

Figure 1:
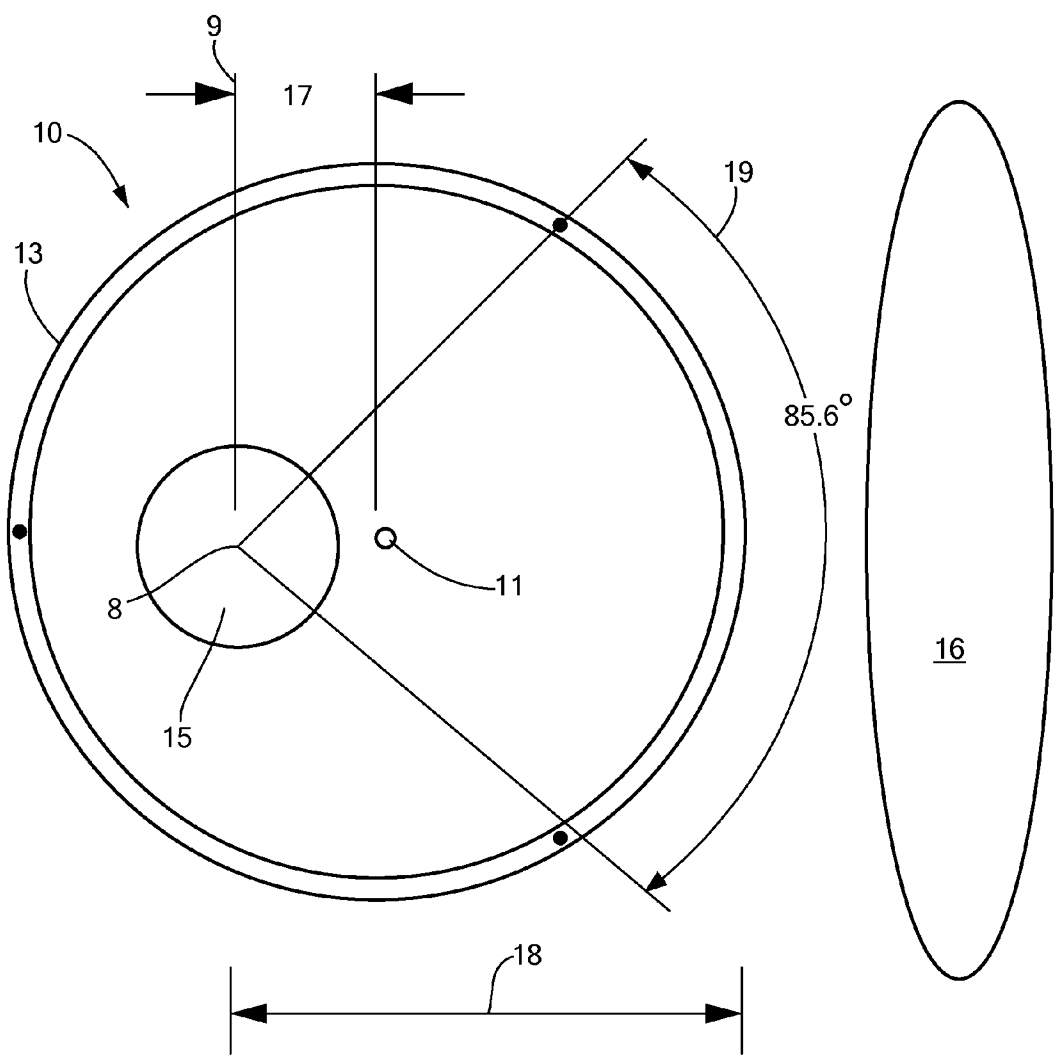
FIG. 1 is a cross-sectional schematic of a prior art beam scanning hoop, with a source of radiation offset rearward of the axis of rotation of the hoop, relative to the object being inspected.
Figure 2:
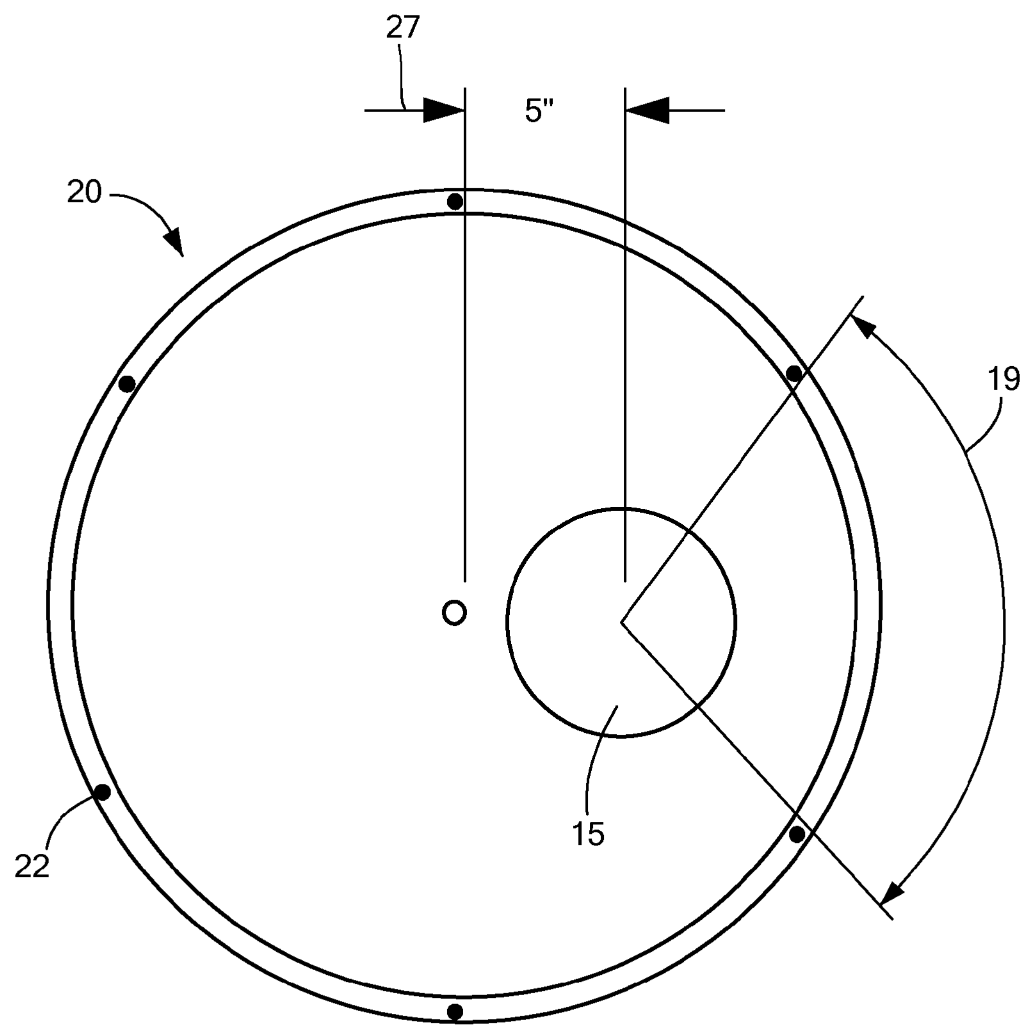
FIG. 2 is a cross-sectional schematic of a forward-offset beam scanning hoop, in accordance with an embodiment of the present invention.

In accordance with embodiments of the present invention, the concept of a forward-offset hoop is presented, a concept which allows the number of apertures to be increased (increased scan lines per rotation and therefore increased scan speed) while still maintaining a FOV sufficient to allow entire vehicles (including trucks) to be imaged. An example of a forward-offset hoop, designated generally by numeral 20, is shown in FIG. 2. Forward-offset hoop 20 is depicted with six apertures 22, although a hoop with any number of apertures, one or greater, is within the scope of the present invention. The forward offset 27 of x-ray tube 15 is 5 inches from the center of the hoop, in the embodiment depicted, and allows a FOV 19 of at least 95 degrees. For the same rotation speed of the hoop, the number of image lines acquired with this hoop is twice that of the hoop shown in FIG. 1.

Figure 3:
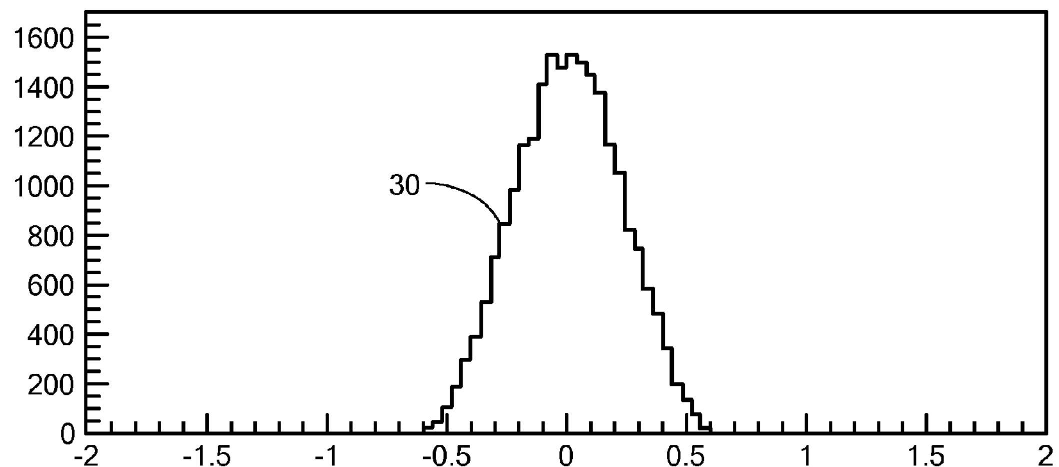
FIG. 3 shows a plot of a simulated cross-section of the beam width of an inspection system for the prior art reverse-offset hoop of FIG. 1.
Figure 4:
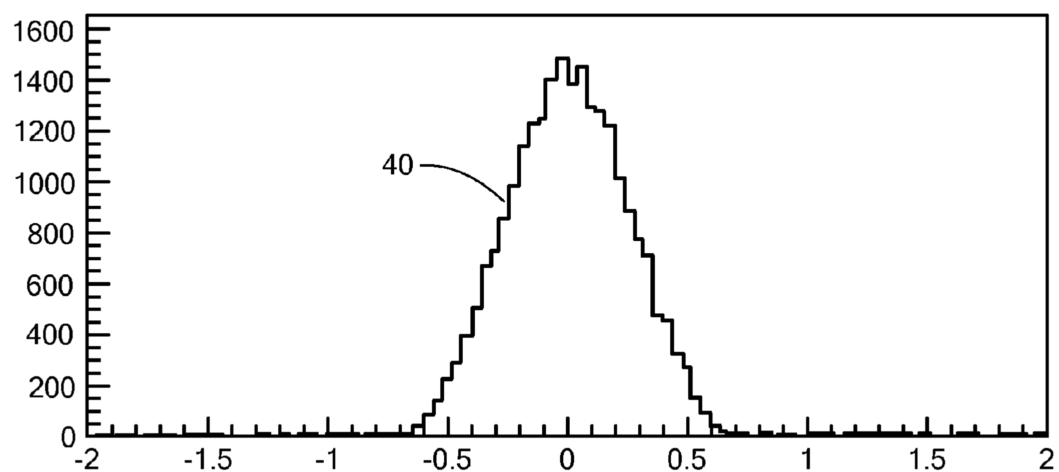
FIG. 4 shows a plot of a simulated cross-section of the beam width of an inspection system for a forward-offset hoop in accordance with an embodiment of the present invention.

Beam profiles of a prior art reverse-offset hoop with a 3.5 mm source focal spot may be compared with beam profiles of a forward-offset hoop with a 1.5 mm source focal spot by reference to the computer simulations of FIGS. 3 and 4. In each case, a 12 inch diameter hoop was used. The beam widths for on-axis illumination of the hoop aperture are shown for the reverse-offset hoop and forward-offset hoop in FIGS. 3 and 4, respectively, based on a scenario of imaging an object 86 inches away from the x-ray tube focal spot. The tube current is the same for each configuration and the apertures of the forward-offset hoop are sized so as to yield the same solid angle (when viewed from the source focal spot) as the reverse-offset hoop. It can be seen that the beam profile is almost identical for the two hoop configurations, as is the flux in the beam per mA.

An alternate embodiment of the invention is now described with reference to FIG. 5. In a variable-offset hoop, designated generally by numeral 50, the source-hoop axis offset 27 is configurable for different imaging applications. Offset configuration may be performed at the factory, with the offset and number of apertures being configured depending on the system the hoop is to be used in. Alternatively, it may be changed dynamically during the course of operation of the system, depending on the size and distance of the object being scanned. For example, for applications where scan speed is not an issue and a highly collimated beam (high image resolution) is desired, a reverse-offset may be configured in the hoop. For high-speed scanning applications, the offset may be changed to a forward-offset. For intermediate applications, tube 15 may also have a zero offset, with the tube positioned at the hoop center 11 (shown in FIG. 1).

Figure 5:
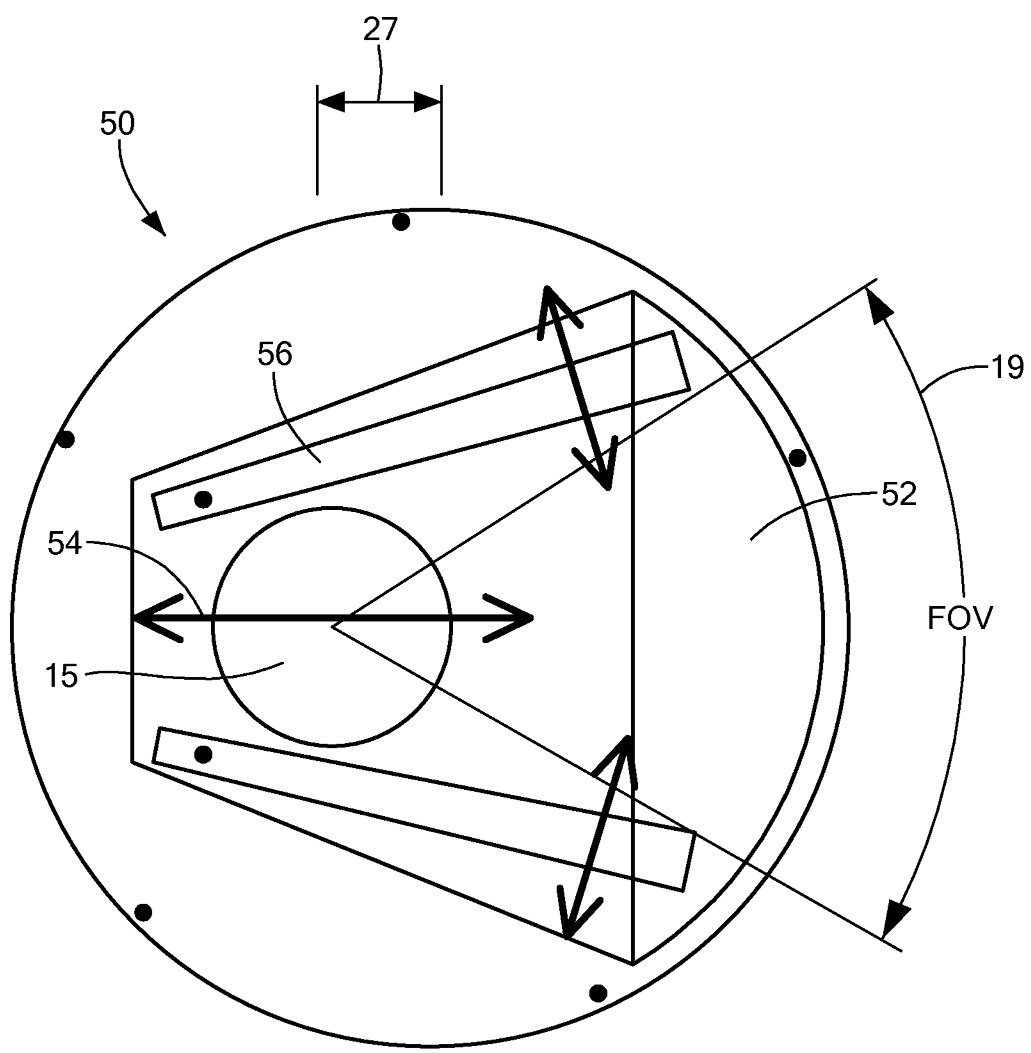
FIG. 5 shows a hoop which is designed to allow for a variable offset.

The embodiment of the invention depicted schematically in FIG. 5 is a factory-configurable hoop 50 with a tube offset 27 that can be set at the factory depending on the system that the hoop is to be mounted in. Source 15 (here, an x-ray tube) is located within a collimator structure 52 and can slide from left to right, along arrow 54, within the collimator structure 52 to adjust the offset 27 (either forward- or reverse). Once the position of source 15 is adjusted, source 15 is locked in place at the desired location. Two moveable shielding devices, such as rotatable shielding arms 56, shown above and below the tube, may be moved within collimator structure 52 in order to increase or decrease the angle of the fan beam of radiation that is emitted from the collimator. Once the desired fan angle is obtained, the shielding arms are locked in place. The mechanism shown in FIG. 5 is shown by way of example only, and many other variations of mechanism that produce similar results are included in the scope of this disclosure.

Table I, below, shows the FOV that is obtained for a given forward-offset for a 30-cm radius hoop with six apertures. Also shown is the "collimation length," which, as defined above, is the distance from the tube focal spot to the defining aperture in the rim of the hoop. For a non-zero forward-offset, the collimation length is larger for the off-axis beam position (with beam aperture at the extremes of the FOV) than for the on-axis position (beam aperture at the center of the FOV). The divergence of the beam is reduced for larger collimation distances (resulting in higher image resolution), but the intensity of the beam (number of x-rays/second) is reduced by the inverse square of the collimation distance for a fixed aperture size. The offset that is used, therefore, is a tradeoff between the desired FOV, the image resolution for scanning an object at a given distance, and the intensity of the beam which determines the signal to noise (or "graininess") of the image.

TABLE I

| Offset | FOV | Collimation length [cm] | |
|---|---|---|---|
| [cm] | [deg] | On-Axis | Off-Axis |
| 0 | 60 | 29.5 | 29.5 |
| 1 | 62 | 28.5 | 28.6 |
| 2 | 64.12 | 27.5 | 27.8 |
| 3 | 66.38 | 26.5 | 26.9 |
| 4 | 68.79 | 25.5 | 26.1 |
| 5 | 71.34 | 24.5 | 25.3 |
| 6 | 74.07 | 23.5 | 24.5 |
| 7 | 76.99 | 22.5 | 23.7 |
| 8 | 80.1 | 21.5 | 22.9 |
| 9 | 83.43 | 20.5 | 22.2 |
| 10 | 86.98 | 19.5 | 21.4 |
| 11 | 90.79 | 18.5 | 20.7 |
| 12 | 94.87 | 17.5 | 20 |
| 13 | 99.22 | 16.5 | 19.4 |
| 14 | 103.89 | 15.5 | 18.7 |
| 15 | 108.86 | 14.5 | 18.1 |
| 16 | 114.17 | 13.5 | 17.6 |
| 17 | 119.81 | 12.5 | 17.1 |
| 18 | 125.8 | 11.5 | 16.6 |

The described embodiments of the invention are intended to be merely exemplary and numerous variations and modifications will be apparent to those skilled in the art. All such variations and modifications are intended to be within the scope of the present invention as defined in the appended claims.

We claim:

1. An apparatus for forming a beam of energetic particles and for scanning the beam of particles with respect to an inspected object, the apparatus comprising:
- a. a source of energetic particles characterized by an effective beam origin;
- b. a rotating hoop having at least one aperture, the rotating hoop characterized by an axis of rotation; and
- c. a collimating structure disposed interior to the rotating hoop for collimating emission by the source into a fan beam prior to impinging on the rotating hoop, wherein the effective beam origin of the source is closer to the inspected object than the axis of rotation of the rotating hoop.

2. An apparatus in accordance with claim 1, wherein the effective beam origin is a target of an x-ray tube.

3. An apparatus in accordance with claim 1, wherein the effective beam origin is adapted to be moved with respect to the axis of rotation of the rotating hoop.

4. An apparatus in accordance with claim 1 wherein the collimating structure includes a plurality of moveable shielding devices for varying an angle of the fan beam emitted from the collimating structure.

5. An apparatus in accordance with claim 3, wherein the effective beam origin is adapted to be moved with respect to the axis of rotation of the rotating hoop during the course of inspection operation.

* * * * *